United States Patent [19]

Miller

[11] Patent Number: 4,889,932
[45] Date of Patent: Dec. 26, 1989

[54] STABILIZED LEUCO PHENAZINE DYES AND THEIR USE IN AN IMAGING SYSTEM

[75] Inventor: Alan G. Miller, St. Paul, Minn.

[73] Assignee: Minnesota Mining and Manufacturing Company, St. Paul, Minn.

[21] Appl. No.: 153,264

[22] Filed: Feb. 8, 1988

Related U.S. Application Data

[63] Continuation-in-part of Ser. No. 911,260, Sep. 15, 1986, abandoned, which is a continuation-in-part of Ser. No. 656,587, Oct. 1, 1984, abandoned.

[51] Int. Cl.$^4$ .................... C07D 241/46; B41M 5/26; B41M 5/12; C09B 17/02
[52] U.S. Cl. ..................................... 544/348; 430/338
[58] Field of Search ........................................ 544/348

[56] References Cited

U.S. PATENT DOCUMENTS

| | | | |
|---|---|---|---|
| 2,783,227 | 2/1957 | Adams et al. | 260/243 |
| 2,783,228 | 2/1957 | Adams et al. | 260/243 |
| 3,873,340 | 9/1975 | Miyazawa et al. | 117/36.8 |
| 4,309,255 | 1/1982 | Gentler et al. | 204/2 |
| 4,379,835 | 4/1983 | Lowrey et al. | 430/338 |
| 4,386,154 | 5/1983 | Smith et al. | 430/336 |
| 4,423,139 | 12/1983 | Isbrandt et al. | 430/338 |
| 4,460,677 | 7/1984 | Smith et al. | 430/336 |

FOREIGN PATENT DOCUMENTS

| | | |
|---|---|---|
| 181085 | 1/1085 | European Pat. Off. |
| 2154659 | 5/1972 | Fed. Rep. of Germany |
| 2154660 | 5/1972 | Fed. Rep. of Germany |
| 52-25330 | 7/1977 | Japan |
| 81-01757 | 6/1981 | PCT Int'l Appl. |
| 1271289 | 4/1972 | United Kingdom |

OTHER PUBLICATIONS

Miller et al, Chem. Abs. 105, 105822j (5-14-86).

Search Report for European Patent Application 85306998.7.

*Primary Examiner*—Mark L. Berch
*Attorney, Agent, or Firm*—Donald M. Sell; Walter N. Kirn; David L. Weinstein

[57] ABSTRACT

3,7-Diamino phenazine leuco dyes stabilized in the 10-position with acyl substituents, said acyl substituents being themselves substituted with electron withdrawing groups. The structure of the reduced form of the dye can be represented by the general formula:

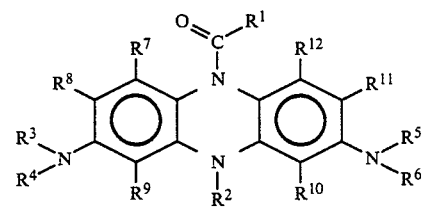

wherein $R^1$ represents a member selected from the group consisting of aryl groups having up to 14 carbon atoms and containing from 1 to 5 electrons withdrawing substituents, alkyl groups having up to 4 carbon atoms and containing one or more electron withdrawing groups, certain electron withdrawing groups containing a

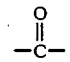

moiety, and certain electron withdrawing groups containing a —NH— moiety. These dyes are suitable for use in thermographic imaging systems wherein the leuco dye is in a composition containing a nitrate salt.

5 Claims, No Drawings

STABILIZED LEUCO PHENAZINE DYES AND THEIR USE IN AN IMAGING SYSTEM

BACKGROUND OF THE INVENTION

This is a continuation-in-part of U.S. Ser. No. 911,260, filed Sept. 15, 1986 abandoned which is a continuation-in-part of U.S. Ser. No. 656,587, filed Oct. 1, 1984 abandoned.

This invention relates to leuco dyes, and more particularly, to stabilized leuco phenazine dyes.

It is well known that dyes in their reduced leuco form can provide the basis of color image forming systems. The leuco dyes may initially be relatively colorless, but can return to a colored form when oxidized, e.g., by nitrate salts in the presence of heat. Examples of leuco dyes used in color image forming systems include triarylmethanes, xanthenes, styryl dyes, and azine dyes, such as, for example, phenazines, phenoxazines, and phenothiazines.

It is also known that the leuco form of a given dye may suffer from instability under ambient conditions and can often revert spontaneously to the colored form of the dye. Among the best of the leuco dyes with respect to thermal and photochemical stability are the phenoxazine and phenothiazine dyes. However, the phenoxazine and phenothiazine dyes are normally restricted to blue and turquoise colors. The phenazine leuco dyes are considerably less stable than the phenoxazine and phenothiazine dyes. However, phenazine dyes are capable of providing yellow, orange, red, and magenta colors. It would be extremely desirable to obtain stable leuco derivatives of the phenazine class in order to provide Yellow, orange, red, magenta, and purple dye forms.

In previous thermographic systems based on combinations of leuco dyes and nitrate salts, at least two approaches have been applied to address the problem of stability to both thermal and actinic effects. The thermal effect, with respect to thermographic processes for preparing transparencies for overhead projection, refers to the problem of attaining the highest possible thermal speed difference between temperatures ranging from 100° C. to 200° C., which range is typical of the temperatures required for image exposure, and temperatures ranging from 25° C. to 60° C., which range is typical of the temperatures on the projector stage after prolonged operation. The actinic effect refers to problems associated with the high light intensity to which the finished transparency is subjected on the projector stage.

One approach involves adding to the imaging system stabilizing compounds, which, in most cases, are normally mild antioxidants, such as, for example, phenidone or ascorbic acid. A second approach involves altering the structure of the leuco dye. Although the first approach has sometimes been successful, it often leads to loss of sensitivity at the temperatures required for image exposure. In many cases, it is not effective at all. Therefore, the second approach is preferable.

Examination of the prior art indicates that acylated (benzoylated) leuco azine dyes exhibit improved stability compared with the hydrogen leuco form thereof. Benzoylated leuco forms of phenoxazines and phenothiazines often show extremely good stability; however, benzoylated leuco phenazine dyes are still far too unstable to be useful for most types of thermally imageable compositions.

SUMMARY OF THE INVENTION

This invention provides 3,7-diamino phenazine leuco dyes with acyl substituents in the 10-position, said acyl substituents being themselves substituted with electron-withdrawing groups. The acyl substituent in the 10-position may also be substituted with electron-donating groups so long as the acyl substituent is electron-withdrawing overall. Incorporation of electron-withdrawing groups on the acyl substituent at the 10-position of the leuco dye such that it is electron-withdrawing overall results in a dramatic improvement in the thermal and light stability of the leuco form, and, generally, the stronger the electron-withdrawing character of the acyl substituent, the more stable is the leuco form. Examples of these substituted acyl substituents include alkylsulfonyl benzoyl, arysulfonylbenzoyl, halobenzoyl, cyanobenzoyl, nitrobenzoyl, and trifluoroalkylbenzoyl.

The leuco dyes of this invention exhibit increased stability to both thermal and actinic effects compared to leuco phenazine dyes heretofore known. The dyes cover a wide range of colors when oxidized, including reds, yellows, and magentas, and they are readily capable of being incorporated into thermographic and photothermographic imaging systems.

In another aspect, this invention relates to thermally imageable compositions comprising the aforementioned stabilized leuco dyes and nitrite salts in which the application of heat causes the reduced, relatively colorless form of the leuco dye to be oxidized to the colored dye form.

DETAILED DESCRIPTION

The thermographic systems of this invention comprise a leuco dye which is capable of being oxidized to give a change in color, a nitrate salt, wherein the cation of the nitrate salt does not react with the leuco dye, and a binder. The leuco dye is a reduced form of a dye with a phenazine nucleus. As used herein, the term "change in color" includes both (1) the case involving a change from an uncolored state (optical density less than 0.2) to a colored state having an optical density of 0.2 units greater than the uncolored state, and (2) the case involving a substantial change in hue, either with or without a substantial change in optical density.

The structure of the reduced form of the dye is represented by the following general formula:

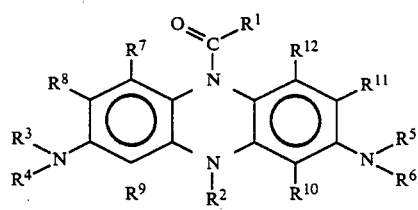

wherein $R^1$ represents a member selected from the group consisting of:
  I. aryl groups having up to 1 carbon atoms and containing from 1 to 5 electron withdrawing substituents, wherein said electron withdrawing substituents are selected from the group consisting of either:
    A. substituents which are overall electron withdrawing independent of their position on the aryl radical, said electron withdrawing substituents being selected from the group consisting of:

1. $-SO_2R^{16}, -SO_2R^{17}, -SO_2N\begin{smallmatrix}R^{14}\\R^{13}\end{smallmatrix}$ 2. 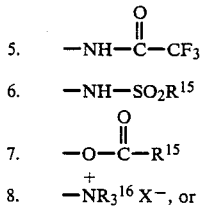

3. $-\overset{\overset{O}{\|}}{C}-OR^{16}, -\overset{\overset{O}{\|}}{C}-OR^{17}$ 4. fluorinated alkyl groups having up to 10 carbon atoms 5. $-NH-\overset{\overset{O}{\|}}{C}-CF_3$

6. $-NH-SO_2R^{15}$

7. $-O-\overset{\overset{O}{\|}}{C}-R^{15}$

8. $-NR_3^{16}\ X^-$, or

B. Substituents which are electron withdrawing inductively but electron donating via resonance, said substituents being located on the ring or rings so as not to be in resonance with the acyl carbonyl, and being selected from the group consisting of

1. $-OR^{16}, -OR^{17}$

2. $-NH-\overset{\overset{O}{\|}}{C}-R^{15}$

II. alkyl groups having up to 4 carbon atoms and containing one or more electron withdrawing groups selected from the group consisting of halogens, $NO_2$, $SO_2R^{15}$, and $OR^{14}$, III. $-\overset{\overset{O}{\|}}{C}-R^{16}, -\overset{\overset{O}{\|}}{C}-R^{17} -\overset{\overset{O}{\|}}{C}-N\begin{smallmatrix}R^{14}\\R^{13}\end{smallmatrix}$ IV. $-\overset{\overset{O}{\|}}{C}-OR^{16}, -\overset{\overset{O}{\|}}{C}-OR^{17}$ V. $-NH-\overset{\overset{O}{\|}}{C}-CF_3$

VI. $-NHSO_2R^{15}$, $R^2$ represents a member selected from unsubstituted alkyl and aryl groups having up to 10 carbon atoms and substituted alkyl or aryl groups having up to 10 carbon atoms, wherein said substituents on said alkyl groups are selected from the group consisting of halogens, hydroxyl, methoxy, and ethoxy, and said substituents on said aryl groups are selected from the group consisting of $R^{14}$, $OR^{14}$,

and halogen, $R^3$, $R^4$, $R^5$ and $R^6$ represent members independently selected from the group consisting of $-\overset{\overset{O}{\|}}{C}-R^{17},$ and $-\overset{\overset{O}{\|}}{C}-N\begin{smallmatrix}R^{14}\\R^{13}\end{smallmatrix}$ and substituted and unsubstituted alkyl groups having up to 1 to 4 carbon atoms wherein said substituents are selected from halogens, $-CN, -NO_2, -OR^{16}, -OR^{17}, -O-\overset{\overset{O}{\|}}{C}-R^{15}, -SO_2R^{16},$ $-SO_2R^{17}, -SO_2N\begin{smallmatrix}R^{14}\\R^{13}\end{smallmatrix} -\overset{\overset{O}{\|}}{C}-OR^{16}, -\overset{\overset{O}{\|}}{C}-OR^{17},$ $-\overset{\overset{O}{\|}}{C}-R^{16}, -\overset{\overset{O}{\|}}{C}-R^{17}, -\overset{\overset{O}{\|}}{C}-N\begin{smallmatrix}R^{14}\\R^{13}\end{smallmatrix},$ $R^7$, $R^8$, $R^9$, $R^{10}$, $R^{11}$ and $R^{12}$ represent members independently selected from the group consisting of hydrogen, halogen, unsubstituted alkyl groups having 1 to 6 carbon atoms, unsubstituted alkoxy groups having 1 to 6 carbon atoms, substituted alkyl groups having 1 to 6 carbon atoms, substituted alkoxy groups having 1 to 6 carbon atoms, wherein substituents on said substituted alkyl groups and alkoxy groups are halogens, $R^{13}$ and $R^{14}$ independently represent a member selected from the group consisting of hydrogen and unsubstituted alkyl groups having up to 10 carbon atoms, $R^{15}$ represents a member selected from the group consisting of unsubstituted alkyl or aryl groups having up to 10 carbon atoms, $R^{16}$ represents a member selected from the group consisting of hydrogen and unsubstituted alkyl groups having up to 16 carbon atoms, $R^{17}$ and $R^{18}$ independently represent a member selected from the group consisting of substituted alkyl or aryl groups having up to 10 carbon atoms, and having up to 3 substituents wherein said substituents are selected from the group consisting of halogen, CN, $NO_2$, alkyl groups having up to 6 carbon atoms, hydroxyalkyl groups having up to 6 carbon atoms, and alkoxy groups having up to 6 carbon atoms.

$X^-$ represents a halogen ion.

As used herein, the term "electron-withdrawing substituent" means a group having a Hammett Sigma Parameter ($\sigma$) value greater than zero (Lange's Handbook of Chemistry, 12th ed., McGraw-Hill, N.Y., 1979 (pp. 3-134 to 3-137), incorporated herein by reference.

$R^1$ is preferably a phenyl or a naphthyl radical having at least one electron-withdrawing group as a substituent thereon. $R^1$ can also be an alkyl radical preferably having 1 to 10 carbon atoms. $R^1$ must have at least one electron-withdrawing group as a substituent thereon. Examples of electron-withdrawing groups include halogen, e.g. chlorine, fluorine, bromine, alkylsulfonyl, e.g. methanesulfonyl; arylsulfonyl, e.g. phenylsulfonyl; nitro; cyano; trifluoroalkyl, e.g., trifluoromethyl.

In addition to the electron withdrawing groups, $R^1$ may also have electron donating groups as substituents, provided that said electron donating substituent groups are not so numerous or so strongly electron donating as to overcome the effect of the electron withdrawing groups, thereby causing $R^1$ to be electron donating overall, rather than electron withdrawing overall. Generally, $R^1$ is likely to remain electron withdrawing overall if the number of electron donating groups present does not exceed the number of electron withdrawing groups present, provided that the Hammett parameter of the electron donating group is not more negative than about $-0.1$, further provided that when said substituent groups are electron donating by resonance, they are positioned so as not to be in resonance with the acyl carbonyl group in the 10-position. Such positioning would greatly enhance the electron donating effect of said substituents, in a manner well known to those skilled in the art. More particularly, electron donating groups selected from the group consisting of alkyl groups having 1 to 16 carbon atoms are permitted in numbers not exceeding the number of electron withdrawing groups present, provided that said alkyl groups are positioned so as not to be in resonance with the acyl carbonyl, as would be apparent to one skilled in the art.

Where $R^2$ is an alkyl group, it is preferred that it contain 1 to 10 carbon atoms. Where $R^2$ is an aryl group, it is preferred that it be a phenyl group or a naphthyl group. Whether aryl or alkyl, $R^2$ can contain various substituents so long as they are inert to the thermographic system and not injurious to quality of the Where $R^3$, $R^4$, $R^5$, or $R^6$ is an alkyl group, it is preferred that it contain 1 to 4 carbon atoms. When $R^3$, $R^4$, $R^5$, or $R^6$ is an alkyl group, it can contain various substituents so long as they are inert to the thermographic system and are not injurious to quality of the image. Examples of such substituents include halogen, such as chloride, bromide, fluoride, and iodide, hydroxy, and alkoxy, said alkoxy preferably having 1 to 10 carbon atoms. Where $R^{16}$, $R^{17}$, or $R^{18}$ is aryl, it is preferably phenyl or naphthyl. Where $R^{16}$, $R^{17}$, or $R^{18}$ is alkyl, it preferably contains 1 to 10 carbon atoms. When $R^{16}$, $R^{17}$, or $R^{18}$ is substituted, it preferably is substituted with at least one electron-withdrawing group.

Where $R^7$, $R^8$, $R^9$, $R^{10}$, $R^{11}$, or $R^{12}$ is an alkyl or an alkoxy group, it is preferred that it contain 1 to 6 carbon atoms. Where $R^7$, $R^8$, $R^9$, $R^{10}$, $R^{11}$, or $R^{12}$, are substituted alkyl or substituted alkoxy groups, it is preferred that the substituents be halogens.

Leuco dyes that are within the scope of the present invention are shown in the following table.

TABLE I

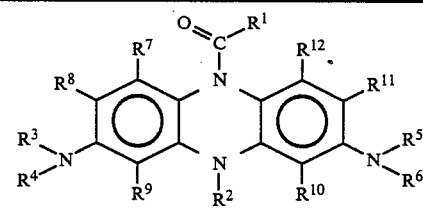

| Leuco Dye | $R^1$ | $R^2$ | $R^3$ | $R^4$ | $R^5$ | $R^6$ | $R^7,R^8,R^9,R^{10},R^{11},R^{12}$ |
|---|---|---|---|---|---|---|---|
| 1 | –C₆H₄–Cl | –C₆H₅ | $-C_2H_5$ | $-C_2H_5$ | $-C_2H_5$ | $-C_2H_5$ | H |
| 2 | –C₆H₃(Cl)₂ (2,4) | –C₆H₅ | $-C_2H_5$ | $-C_2H_5$ | $-C_2H_5$ | $-C_2H_5$ | H |
| 3 | –C₆H₃(Cl)₂ | $-C_2H_5$ | $-C_2H_5$ | $-C_2H_5$ | $-C_2H_5$ | $-C_2H_5$ | H |
| 4 | –C₆H₄–Br | –C₆H₅ | $-C_2H_5$ | $-C_2H_5$ | $-C_2H_5$ | $-C_2H_5$ | H |
| 5 | –C₆H₄–F | –C₆H₅ | $-C_2H_5$ | $-C_2H_5$ | $-C_2H_5$ | $-C_2H_5$ | H |
| 6 | –C₆H₄–CF₃ | –C₆H₅ | $-C_2H_5$ | $-C_2H_5$ | $-C_2H_5$ | $-C_2H_5$ | H |
| 7 | –C₆H₄–CN | –C₆H₅ | $-C_2H_5$ | $-C_2H_5$ | $-C_2H_5$ | $-C_2H_5$ | H |
| 8 | –C₆H₄–SO₂–C₆H₅ | –C₆H₄–OCH₃ | $-C_2H_5$ | $-C_2H_5$ | $-C_2H_5$ | $-C_2H_5$ | H |
| 9 | –C₆H₄–SO₂–C₆H₅ | –C₆H₅ | $-C_2H_5$ | $-C_2H_5$ | $-C_2H_5$ | $-C_2H_5$ | H |

TABLE I-continued

Structure: Central diphenyl compound with R¹-C(=O)-N bridge, substituents R²-R¹² on positions as shown.

| Leuco Dye | R¹ | R² | R³ | R⁴ | R⁵ | R⁶ | R⁷,R⁸,R⁹,R¹⁰,R¹¹,R¹² |
|---|---|---|---|---|---|---|---|
| 10 | –C₆H₄–SO₂CH₃ | –C₆H₅ | –C₂H₅ | –C₂H₅ | –C₂H₅ | –C₂H₅ | H |
| 11 | –(2,3-dichlorophenyl) | –C₆H₅ | –CH₂CH₂CN | –CH₂CH₂CN | –C(O)–(2,3-dichlorophenyl) | H | H |
| 12 | –C₆H₄–CF₃ | –C₆H₅ | –CH₂CH₂CN | –CH₂CH₂CN | –C(O)–C₆H₄–CF₃ | H | H |
| 13 | –C₆H₄–SO₂–C₆H₅ | –C₆H₅ | –CH₂CH₂CN | –CH₂CH₂CN | –C(O)–C₆H₄–SO₂–C₆H₅ | H | H |
| 14 | –C₆H₄–SO₂–C₆H₅ | –C₆H₅ | –CH₂CH₂CN | –CH₂CH₂CN | –C(O)–C₆H₅ | H | H |
| 15 | –CHCl₂ | –C₆H₅ | –CH₂CH₂CN | –CH₂CH₂CN | –C(O)–CHCl₂ | H | H |
| 16 | –CH₂Cl | –C₆H₅ | –CH₂CH₂CN | –CH₂CH₂CN | –C(O)–CH₂Cl | H | H |
| 17 | –(2,3-dichlorophenyl) | –C₆H₅ | CF₃CH₂– | –CH₂CH₂CN | –C(O)–(2,3-dichlorophenyl) | H | H |
| 18 | –C₆H₄–SO₂–C₆H₅ | CH₃–C₆H₄– | CF₃CH₂– | –CH₃ | CF₃CH₂– | –CH₃ | H |

The dyes of this invention can be prepared by the process described below. A phenylene diamine derivative, e.g., N,N-diethyl-p-phenylenediamine, an aniline derivative, e.g., N,N-diethylaniline, and a strong acid, e.g., HCl, are combined in a solvent, preferably water, in a reaction vessel and stirred, preferably at or below room temperature (25° C.). An oxidizing agent, preferably sodium dichromate, is added to the solution to couple the diamine and aniline derivative. Any aniline derivative having an unsubstituted —NH₂ group or akylamine having an unsubstituted —NH₂ group is then added to the mixture. The resulting mixture is then stirred and optionally heated over a sufficient period of time to bring about formation of the dye product. To the solution is added an ionizable halide salt, e.g., KI, NaCl, to precipitate the dye product. The solution is then cooled, and the dye collected by filtration and dried in air. The leuco form of the dye can be prepared in the following manner. The previously prepared dye is dissolved in a solvent, preferably water. A solvent for the leuco dye to be prepared, e.g. methylene chloride, is added, and the pH is adjusted to about 10. In an inert atmosphere, e.g., nitrogen, the dye is first reduced with sodium dithionite and then acylated with an appropriate acid chloride, e.g., p-(phenylsulfonyl)benzoyl chloride. When the reaction is complete, the solvent layer containing the leuco dye is isolated and treated with a decolorizing agent, e.g., Attapulgus clay. Removal of the solvent yields the leuco dye.

Leuco dyes nos. 1 ∝ 13, 15–18 (Table I) can be prepared by the foregoing method. Leuco dye no. 14 (Table I) can be prepared by coupling 4-[bis-2-(cyanoethyl)amino] aniline with two moles of aniline to give the colored dye form. Reduction and acylation with benzoyl chloride gives the 3,10-dibenzoyl leuco form. Oxidation to the colored dye form with sodium dichromate gives the starting dye material, but with a benzoyl group substituted at the 3-position. Reduction and acylation with p-(phenylsulfonyl-)benzoyl chloride gives leuco dye no. 14.

The leuco dye can be used to prepare thermally imageable compositions which comprise a layer comprising a binder, a stabilized leuco dye, and a nitrate salt in which application of heat causes the reduced, relatively colorless form of the leuco dye to be oxidized to the colored dye form. Upon application of a sufficient amount of heat, e.g. a rise in temperature of from about 25° C. to about 80° C. to 160° C., the leuco dye contained in the thermally imageable composition will exhibit a change in color.

Nitrate salts suitable for this invention are themselves well known. They may be supplied as various chemical compounds, but are desirably provided as a metal salt, and most preferably provided as a hydrated metal salt. Most means of supplying the nitrate salt into the imaging composition are satisfactory. For example, organic salts, metal salts, acid salts, mixtures of acids and salts, and other means of supplying the ion are useful. Nitrates of zinc, cadmium, potassium, calcium, zirconyl ($ZrO_2$), nickel, aluminum, chromium, iron, copper, tin, magnesium, lead, and cobalt, ammonium nitrate, and cerous ammonium nitrate can be used.

The nitrate salt component of the present invention must be present in a form within the imaging composition so that oxidizing quantities of $HNO_3$, $NO$, $NO_2$, or $N_2O_4$ will be provided within the composition when it is heated to a temperature no greater than 320° F. (160° C.) for 60 seconds and preferably no greater than 180° F. (80° C.) for 60 or more preferably 30 seconds. The salt must be chosen so that the cation thereof is non-reactive with the leuco dye. Non-reactive salts are defined in the practice of the present invention as those salts the cations of which do not spontaneously oxidize the dyes with which they are associated at room temperature. This may be readily determined in a number of fashions. For example, the dye and a non-nitrate (preferably halide) salt of the cation may be codissolved in a solution. If the salt oxidizes the dye spontaneously (within two minutes) at room temperature, it is a reactive salt.

Preferred salts are hydrated metal salts such as nickel nitrate hexahydrate, magnesium nitrate hexahydrate, aluminum nitrate nonahydrate, ferric nitrate nonahydrate, cupric nitrate trihydrate, zinc nitrate hexahydrate, cadmium nitrate tetrahydrate, bismuth nitrate pentahydrate, thorium nitrate tetrahydrate, cobalt nitrate hexahydrate, gadolinium or lanthanum nitrate nonahydrate, and mixtures of these hydrated nitrates. Nonhydrated or organic nitrates may be admixed therewith.

It is preferred to have at least 0.10 mole of nitrate ion per mole of dye. It is more preferred to have at least 0.30 or 0.50 mole of nitrate ion per mole of dye. Even amounts of 1.0 mole of nitrate ion per mole of dye can be useful. The nitrate ordinarily constitutes from 0.05 to 10 percent by weight of the imaging composition, preferably 0.1 to 10, and most preferably 0.5 to 8 percent by weight.

The thermally stimulated oxidation of the leuco dye by the nitrate salt can be facilitated by the presence of an acid. The acids optionally useful in the thermographic system of this invention are acids generally known to the skilled chemist. Organic acids, preferably those having carboxylic groups, such as phthalic acid, are preferred, but inorganic acids can also be used. The acid can be present in a ratio of up to 10 times the amount of the nitrate ion. The acid is preferably present as at least about 0.1% by weight of the total weight of the heat sensitive composition. More preferably it is present in amounts from 0.2 to 2.0 times the amount of nitrate ion. The acid may, for example, be present in a range of from 0.05 to 10 percent by weight, preferably from 0.1 to 7 percent, most preferably from 0.5 to 5 percent of the composition.

The leuco dye, nitrate salt, and acid, when employed, are dissolved in a binder, which binder is neither strongly basic nor strongly acidic but which is sufficiently polar to hold the constituents in solution. It is preferred that the binder be selected from polymeric materials. Such resins as polyvinyl acetals, e.g., polyvinyl butyral, polyvinyl resins, polyvinylpyrrolidone, polyesters, polycarbonates, polyamides, polyacrylates, cellulose esters, copolymers and blends of these classes of resins, can be used. Vinyl chloride-vinylidene chloride copolymers, e.g. Saran, are particularly preferred. Natural polymeric materials such as gelatin and gum arabic can also be used. Where the proportions and activities of leuco dyes and nitrate ion require a particular developing time and temperature, the resin should be able to withstand those conditions. Generally, it is preferred that the polymer not decompose or lose its structural integrity at 200° F. (93° C.) for 30 seconds and most preferred that it not decompose or lose its structural integrity at 260° F. (127° C.) for 30 seconds.

The leuco dye should be present as at least 0.3% by weight of the binder, preferably as at least 1% by weight of the binder, and most preferably as from 2 to 10% or more by weight of the binder.

A formulation which can be applied by conventional coating techniques can be produced by dissolving the stablized leuco dye, the nitrate salt, and the polymeric binder, together with the acid, if used, and, optionally, a stabilizing compound, e.g., phenidone, catechol, hydroquinone, and mixtures thereof, in an inert organic solvent, such as, for example, acetone, methyl ethyl ketone, or tetrahydrofuran.

The formulation can be coated onto a support by methods well known in the art, such as, for example, wire-wound rod, knife, or extrusion coating. Typical wet thickness of the layer can range from about 10 to about 100 micrometers ($\mu$m), and the layer can be dried in forced air at temperatures ranging from 20° C. to 50° C. It is preferred that the coating thickness be selected to provide maximum image densities greater than 0.2, and more preferably in the range 0.5 to 1.5, as measured on a MacBeth Color Densitometer Model TD 504 using the color filter complementary to the dye color.

The support material can be selected from a wide range of materials, including paper, glass, polymeric film, and the like, depending upon the particular imaging requirement. Preferred materials include polymers having good heat stability, such as polyesters. A particularly preferred polyester is polyethylene terephthalate.

Further discussion relating to nitrate salts, binders, stabilizers, and other material useful in thermographic imaging systems analogous to the system described herein can be found in U.S. Pat. No. 4,379,835, incorporated herein by reference.

The leuco phenazine dyes of this invention provide several valuable properties, including, for example:
(a) capability of changing color upon application of heat in thermal imaging systems based on oxidation by metal nitrate,
(b) improvement in photochemical stability when coated in a polymeric binder on a film substrate,
(c) improvement in thermal stability when coated in a polymeric binder on a film substrate, (d) improved thermal stability upon oven drying during manufacture, (e) improved thermal stability in the coating solutions, providing extended and useful potlife, (e) provision of colors of the red, yellow and magenta hue, said colors previously being available only with the trade-off of very low stability to heat and radiation.

The following examples serve to illustrate the present invention and should not be deemed to be limitative thereof. All percentages are percent by weight unless otherwise indicated.

EXAMPLE I

This example demonstrates the preparation of 5,10-dihydro-5-phenyl-10-(4-phenylsulfonylbenzoyl)-3,7-di(N,N-diethylamino)phenazine (leuco dye no. 9 of Table I).

Into a 1-liter, 3-neck round-bottom flask equipped with a mechanical stirrer, pH electrode, and an argon inlet and outlet, was added 10.0 g (0.023 M) tetraethylphenosafranine and 200 ml deionized water. The mixture was stirred for several minutes to dissolve the dye as completely as possible. Methylene chloride (40 ml) was then added, and the system was flushed with argon. The pH was adjusted to 10 with 20% aqueous NaOH, and 8.0 g (0.046 M) sodium dithionite was added all at once as a solid. The pH dropped to between about 3-4 and the solution decolorized over several minutes to an olive-green color. The solution was stirred for about 20 minutes. The acid chloride, 9.69 g (0.035 M) p-(phenylsulfonyl)benzoylchloride, ground to a fine powder and suspended in 60 ml methylene chloride, was added dropwise over a period of 30-45 minutes, the pH being adjusted continuously with NaOH solution to keep it between 3 and 4.5.

After the addition of acid chloride, about 25 ml methylene chloride was used to rinse the residual acid chloride into the flask. The mixture was stirred for about 3 hours. The pH was then adjusted to between 9.5 and 10 and the solution was stirred an additional hour. The methylene chloride layer was isolated from the water layer (pH 10) and washed once with 5% NaOH solution. The solution was dried over $CaSO_4$ and the methylene chloride was stripped leaving about 10.36 g (69%) crude product. Decolorizing three times with Attapulgus clay yielded a light yellow-brown methylene chloride solution which, upon removal of solvent, gave about 5.2 g product (35%).

EXAMPLE II

This example demonstrates the preparation of N-[8-[bis(2-cyanoethyl)amino]-5-[4-(phenylsulfonyl)-benzoyl]-5,10-dihydro-10-phenyl-2-phenazinyl]-4-phenylsulfonyl)benzamide (leuco dye no. 13 of Table I) and the preparation of its dye precursor.

A 3-liter round-bottomed flask fitted with a mechanical stirrer was loaded with 16.6 g (0.066 mole) of 4-(bis-2(cyanoethyl)amino) aniline in 800 ml of distilled water. A 10% excess of aniline (13.56 g, 0.1456 mole) and 200 ml of distilled water were added to the mixture. the mixture was cooled to 0° C. in an ice bath, and 10 g concentrated hydrochloric acid in 25 ml of water were added. Then 6.31 g (0.0883 mole) of sodium dichromate in 25 ml of water was added. The temperature rose to 7° C. Stirring was continued as 9 ml of concentrated hydrochloric acid in 25 ml of distilled water was added over a period of two hours. After 16 hours the temperature had risen to 20° C. The mixture was heated under reflux for 4 hours and then filtered hot. The filter cake was washed with 1.5 liters of boiling water. The combined filtrates were concentrated to 1.4 liters by vacuum evaporation, and then heated to 75° C. as 200 g of sodium chloride were added.

The mixture was cooled to room temperature, chilled in an ice bath, and the solid was then recovered by filtration to give 14.6 g (yield=51.6%). ($\lambda$max—537 nm in methanol).

A 1 liter 3 necked flask was fitted with a Claisen head with two dropping funnels, a mechanical stirrer, and a pH electrode. A solution containing 5.0 g (0.012 mole) of the dye prepared above, 210 ml of water and 0.2 g of ethylene diamine tetraacetic acid was added to the flask and stirred, while 250 ml of methylene chloride was added. The system was closed and flushed with argon, the pH adjusted to 10, then 2.44 g (0.014 mole) of sodium dithionite was added. The solution turned orange and the pH dropped to 3.7. Aqueous sodium hydroxide solution (25%) was added to bring the pH to 4.5, and then 7.53 g (0.027 mole) of 4-phenyl sulfonyl benzoyl chloride in 60 ml of methylene chloride was added dropwise. The pH was maintained between 4 and 5. After 1½ hours, the pH was raised to 10-11. After an additional 50 minutes, the methylene chloride layer was removed and dried over calcium sulfate. The solution was treated with about 10 g of Attapulgus clay and filtered. The solvent was then evaporated, leaving 8.14 g of solid (79% yield).

EXAMPLE III

This example demonstrates how thermally imageable films prepared with similar imaging compositions but containing leuco dyes differing only in the substituents at the 10-position, i.e. $R^1$, exhibit differing stabilities on the stage of an overhead projector. The stability of the leuco forms in the imageable films on an overhead projector is directly related to the time that the unimaged areas, i.e. "background" areas, remain relatively low in density. A background density reading of greater than 0.1 on any filter is normally considered the point of failure.

Formulations A and B were prepared by mixing the following ingredients in the amounts indicated:

| Ingredient | Formulation A Amount (g) | Formulation B Amount (g) |
|---|---|---|
| Leuco dye no. 9 (Table I) | 0.05 | — |
| Leuco dye no. 2 (Table I) | — | 0.05 |
| 1% Phenidone in tetrahydrofuran | 0.7 | 0.7 |
| 5% Catechol in tetrahydrofuran | 0.12 | 0.12 |
| Tetrahydrofuran | 3.0 | 3.0 |
| 15% Vinylidene chloride-acrylonitrile copolymer in methyl ethyl ketone (Saran ® F-310, Dow Chemical Company) | 8.0 | 8.0 |
| Phthalic acid | 0.06 | 0.06 |
| $Ni(NO_3)_2$ | 0.12 | 0.12 |
| Nonionic fluorochemical surfactant 1% FC-430 in tetrahydrofuran | 0.20 | 0.20 |

Formulation A was coated at 3 mil (75 μm) wet thickness on a 4 mil (100 μm) polyester film and dried for 3 minutes at 140° F. (60° C.). Formulation B was coated at 3 mil (75 μm) wet thickness on a 4 mil (100 μm) polyester film and dried for 4 minutes at 130° F. (54° C).

Test images were formed by means of infrared imaging in a 3M Model 45 Infrared Transparency Maker.

A 3M Model 66 overhead projector was used in conducting the image stability tests. The Model 66 had a high wattage bulb (615 watts) and gave a relatively high stage temperature (65° C.).

Background image densities were measured with a MacBeth Densitometer Model TD504. Maximum image dye densities of about 1.0 were used in all cases. Background image densities after various periods of time on the stage of the Model 66 overhead projector are recorded in Table II:

TABLE II

| Formulation | Filter | Time (hrs) | | | | |
|---|---|---|---|---|---|---|
| | | 0 | 6 | 8.5 | 19 | 27 |
| A | Yellow | 0.03 | | 0.03 | 0.06 | 0.06 |
| A | Red | 0.03 | | 0.02 | 0.04 | 0.03 |
| A | Green | 0.03 | | 0.02 | 0.06 | 0.06 |
| A | Blue | 0.04 | | 0.04 | 0.05 | 0.05 |
| B | Yellow | 0.04 | 0.06 | | | |
| B | Red | 0.03 | 0.04 | | | |
| B | Green | 0.03 | 0.07 | | | |
| B | Blue | 0.04 | 0.05 | | | |

The p-(phenylsulfonyl)-benzoyl group of leuco dye no. 9 is more electron-withdrawing than the 3,4-dichlorobenzoyl group of leuco dye no. 2 and the stage life of dye no. 9 is much greater than the stage life of leuco dye no. 2.

COMPARATIVE EXAMPLE A

This Example demonstrates the relative instability of the unsubstituted benzo form of the same dye used in Example III i.e. $R^1 =$

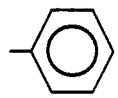

with $R^2$, $R^3$, $R^4$, $R^5$, $R^6$, $R^7$, $R^8$, $R^9$, $R_{10}$, $R^{11}$, $R^{12}$, being identical to those in leuco dyes no. 9 (Table I) and no. 2 (Table I) the stabilities of which were demonstrated in Example III. Formulation C was prepared by mixing the following ingredients in the amounts indicated:

| Ingredient | Formulation C Amount (g) |
|---|---|
| Benzoyl leuco dye of tetraethylphenosafranine | 0.07 |
| 1% Phenidone in tetrahydrofuran | 0.80 |
| 5% Catechol in tetrahydrofuran | 0.18 |
| Tetrahydrofuran | 3.0 |
| 15% Vinylidene chloride-acrylonitrile copolymer (Saran ® F-310) in methyl ethyl ketone | 8.0 |

Formulation C was coated at 3 mil (75 μm) wet thickness on a 4 mil (100 μm) polyester film and dried for 5 minutes at 120° F. (49° C.). This coating was then overcoated with the following composition:

| Ingredient | Amount (g) |
|---|---|
| Ni(NO$_3$)$_2$ | 0.13 |
| p-Toluenesulfonic acid | 0.075 |
| Water | 3.0 |
| 5% Polyvinyl alcohol (Elvanol ® 52-22) | 8.0 |

| Ingredient | Amount (g) |
|---|---|
| in water | |

The overcoat composition was coated at 3 mil (75 μm) wet thickness and dried for 5 minutes at 120° F. (49° C. usable film could be prepared only by coating the nitrate oxidant and the leuco dye in separate layers.

Background image densities after various periods of time on the stage of the Model 66 overhead projector are recorded in Table III.

TABLE III

| Filter | Time (hrs) | | |
|---|---|---|---|
| | 0 | 1 | 3 |
| Yellow | 0.03 | 0.14 | 0.39 |
| Red | 0.02 | 0.03 | 0.05 |
| Green | 0.08 | 0.12 | 0.39 |
| Blue | 0.04 | 0.07 | 0.10 |

Because a background density in excess of 0.10 on any filter is normally considered to indicate the point of failure, from the foregoing Table, it can be seen that stage life is less than one hour. The dye in this comparative example is less stable than the dyes in Example III.

EXAMPLE IV

Leuco dyes no. 11 (Table I) and no. 13 (Table I) were prepared from the same starting dye form, as was the unsubstituted benzoyl leuco form, i.e., where $R^1$ and $R^5$ are

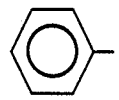

and $R^2$, $R^3$, $R^4$ and $R^6$ are identical to those substituents in leuco dyes no. 11 and no. 13. The starting dye form is shown below:

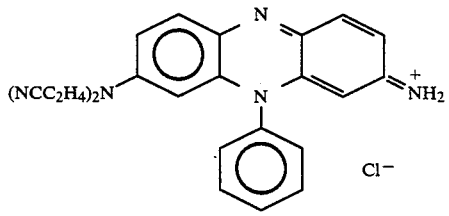

The unsubstituted benzoyl leuco dye could be coated without backgrounding only by adding diphenylamine to the formulation. The coating formulations for the unsubstituted benzoyl leuco dye and for leuco dyes no. 11 and no. 13 are set forth below:

| Ingredient | Formulation D Amount (g) | Formulation E Amount (g) | Formulation F Amount (g) |
|---|---|---|---|
| Unsubstituted benzoyl leuco dye | 0.017 | | |
| Leuco dye no. 11 (Table I) | | 0.015 | |
| Leuco dye no. 13 (Table I) | | | 0.02 |
| 1% Phenidone in tetrahydrofuran | 0.2 | 0.13 | 0.2 |
| 5% Catechol in tetrahydrofuran | 0.04 | 0.023 | 0.037 |

-continued

| Ingredient | Formulation D Amount (g) | Formulation E Amount (g) | Formulation F Amount (g) |
|---|---|---|---|
| Phthalic acid | 0.015 | 0.010 | 0.015 |
| Tetrahydrofuran | 0.5 | 0.3 | 0.5 |
| Diphenylamine | 0.009 | | |
| Ni(NO$_3$)$_2$.6H$_2$O | 0.03 | 0.022 | 0.03 |
| 15% Vinylidene chloride-acrylonitrile copolymer (Saran ® F-310) in methyl ethyl ketone | 2.0 | 1.12 | 2.0 |

Formulations D and F were coated onto 4 mil (100 μm) polyester film at 3 mil (75 μm) wet thickness and dried at 120° F. (49° C.) for 5 minutes. Formulation E was coated onto 4 mil (100 μm) polyester film at 3 mil (75 μm) wet thickness and dried at 132° F. (56° C.) for 4 minutes.

Background image densities after various periods of time on the stage of the Model 66 overhead projector are recorded in Table IV:

TABLE IV

| Leuco dye | Filter | Time (hrs) | | | | | |
|---|---|---|---|---|---|---|---|
| | | 0 | 1 | 2 | 6 | 9 | 16 |
| Unsubstituted benzoyl | Yellow | .04 | .09 | | | | |
| | Red | .04 | .05 | — | — | — | — |
| | Green | .04 | .13 | | | | |
| | Blue | .05 | .09 | | | | |
| 11 | Yellow | .03 | .04 | .04 | .07 | | .08 |
| | Red | .03 | .04 | .03 | .04 | | .04 |
| | Green | .03 | .05 | .05 | .08 | | .11 |
| | Blue | .05 | .06 | .07 | .08 | | .09 |
| 13 | Yellow | .03 | | | | | .05 |
| | Red | .03 | — | — | — | — | .04 |
| | Green | .03 | | | | | .05 |
| | Blue | .07 | | | | | .09 |

Even with the additional stabilizer present, the stage life of Formulation D was less than 1 hour. The 3,4-dichlorobenzoyl leuco dye of Formulation E was of intermediate stability, showing backgrounding after 6 hours. The p-phenylsulfonyl benzoyl leuco dye of Formulation F showed the greatest stability. Although the image density on the blue filter had a high initial value, it changed only slightly after 16 hours on the stage.

EXAMPLE V

This example demonstrates that in leuco dyes of the present invention having acyl groups at positions $R^5$ and $R^1$ (of Formula I), the electron-withdrawing substituent at position 10, i.e., $R^1$, is most responsible for the enhanced stability of the leuco dye. In the formulations described below, a small amount of yellow leuco dye 2,3-dihydro-1,3,3-trimethyl-2-[2-(2,4,6-trimethoxyphenyl) ethenyl]-1H-indole, was added to each formulation to alter the image color. The coating formulations were as follows:

| Ingredient | Formulation G Amount (g) | Formulation H Amount (g) |
|---|---|---|
| Leuco dye no. 13 (Table I) | 0.20 | — |
| Leuco dye no. 14 (Table I) | — | 0.014 |
| Yellow leuco dye | 0.002 | 0.002 |
| 1% Phenidone in tetrahydrofuran | 0.23 | 0.23 |
| Diphenylamine | 0.003 | 0.003 |
| Phthalic acid | 0.015 | 0.015 |
| Tetrahydrofuran | 0.35 | 0.35 |
| Ni(NO$_3$)$_2$.6H$_2$O | 0.03 | 0.03 |
| 15% Vinylidene chloride-acrylonitrile copolymer (Saran ® F-310) in methyl ethyl ketone | 1.60 | 1.60 |

Formulations G and H were coated onto 4 mil (100 μm) polyester film at 3 mil (75 μm) wet thickness and dried at 165° F. (74° C.) for two minutes. Background image densities as a function of time on the stage of the Model 66 overhead projector are shown in Table V.

TABLE V

| Leuco dye | Filter | Time (hrs) | | |
|---|---|---|---|---|
| | | 0 | 8 | 21 |
| 13 | Yellow | .04 | .04 | .07 |
| | Red | .03 | .03 | .05 |
| | Green | .04 | .05 | .08 |
| | Blue | .09 | .10 | .12 |
| 14 | Yellow | .03 | .04 | .05 |
| | Red | .03 | .03 | .04 |
| | Green | .03 | .04 | .06 |
| | Blue | .09 | .09 | .10 |

Leuco dye no. 14 is essentially identical to leuco dye no. 13 with respect to stability, even though the benzoyl group at the 3-position ($R^5$) does not contain an electron-withdrawing substituent.

EXAMPLE VI

This Example demonstrates that the leuco dyes of the present invention exhibit increased stability in the coating formulations themselves, in addition to exhibiting increased stability to both thermal and actinic effects when coated on a substrate. In other words, the "pot-life" of the coating formulations for leuco phenazines dyes containing strong electron-withdrawing groups at the 10-position is longer than the "pot-life" of coating formulations containing leuco phenazine dyes that have weak electron-withdrawing substituents at the 10-position. The following formulations were prepared to illustrate this feature.

| Ingredient | Formulation | | | | | |
|---|---|---|---|---|---|---|
| | J Amount (g) | K Amount (g) | L Amount (g) | M Amount (g) | N Amount (g) | O Amount (g) |
| Unsubstituted benzoyl leuco of tetraethylphenosafranine | 0.60 | — | — | — | — | — |
| Leuco dye no. 4 (Table I) | — | .065 | — | — | — | — |
| Leuco dye no. 2 (Table I) | — | — | .065 | — | — | — |
| Leuco dye no. 6 (Table I) | — | — | — | .065 | — | — |
| Leuco dye no. 7 (Table I) | — | — | — | — | .062 | — |
| Leuco dye no. 9 (Table I) | — | — | — | — | — | .07 |
| 1% Phenidone in tetrahydrofuran | .80 | .80 | .80 | .80 | .80 | .80 |

| | Formulation | | | | | |
|---|---|---|---|---|---|---|
| Ingredient | J Amount (g) | K Amount (g) | L Amount (g) | M Amount (g) | N Amount (g) | O Amount (g) |
| 5% Catechol in tetra-hydrofuran | .14 | .14 | .14 | .14 | .14 | .14 |
| Phthalic acid | .06 | .06 | .06 | .06 | .06 | .06 |
| Tetrahydrofuran | 3.0 | 3.0 | 3.0 | 3.0 | 3.0 | 3.0 |
| Ni(NO$_3$)$_2$.6H$_2$O | .11 | .11 | .11 | .11 | .11 | .11 |
| 15% Vinylidene chloride-acrylonitrile copolymer in methyl ethyl ketone | 8.0 | 8.0 | 8.0 | 8.0 | 8.0 | 8.0 |

The approximate pot lives of the formulations are listed in Table VI.

| Formulation | Pot Life |
|---|---|
| J | <15 min |
| K | 1 hr |
| L | several hours |
| M | several days |
| N | about 2 weeks |
| O | about 2 weeks |

Various modifications and alterations of this invention will become apparent to those skilled in the art without departing from the scope and spirit of this invention and it should be understood that this invention is not to be unduly limited to the illustrative embodiments set forth herein.

What is claimed is:

1. A leuco phenazine dye having the structural formula:

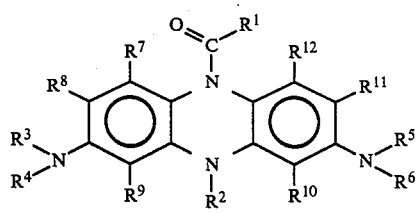

wherein $R^1$ represents a member selected from the group consisting of:

I. aryl groups having up to 10 carbon atoms and containing from 1 to 5 electron withdrawing substituents, wherein said electron withdrawing substituents are selected from the group consisting of either:

A. sustituents which are overall electron withdrawing independent of their position on the aryl radical, said electron withdrawing substituents being selected from the group consisting of:
1. —SO$_2$R$_{17}$
2. trifluoroalkyl groups having up to 10 carbon atoms II. alkyl groups selected from the group consisting of —CH$_2$Cl and —CHCl$_2$, R$_2$ represents a member selected from unsubstituted alkyl and aryl groups having up to 10 carbon atoms and substituted alkyl and aryl groups having up to 10 carbon atoms, wherein said substituents on said alkyl groups can be methoxy groups and said substituents on said aryl groups can be selected from the group consisting of methoxy and methyl, R$_3$, R$_4$, R$_5$ and R$_6$ independently represent members selected from the group consisting of:

and substituted and unsubstituted alkyl groups having 1 to 6 carbon atoms wherein said substituents are selected from the group consisting of halogens, —CN, hydroxy, and alkoxy having 1 to 10 carbon atoms, R$^7$, R$^8$, R$^9$, R$^{10}$, R$_{11}$ and R$^{12}$ independently represent members selected from the group consisting of hydrogen, halogen, unsubstituted alkyl groups, unsubstituted alkoxy groups having up to 4 carbon atoms, substituted alkyl groups having up to 4 carbon atoms, and substituted alkoxy groups having up to 4 carbon atoms, wherein said substitutents are selected from halogen, and R$^{17}$ represents a member selected from the group consisting of unsubstituted alkyl and aryl groups having up to 10 carbon atoms.

2. The leuco phenazine dye of claim 1 wherein said electron withdrawing substituent is:
—SO$_2$R$^{17}$.

3. The leuco phenazine dye of claim 1 wherein said electron withdrawing groups are fluorinated alkyl groups having up to 10 carbon atoms.

4. The leuco phenazine dye of claim 1 wherein R$^1$ represents

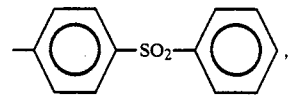

R$^2$ represents

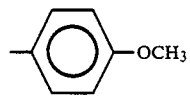

R$^3$, R$^4$, R$^5$, R$^6$ represents unsubstituted alkyl groups having 1 to 4 carbon atoms, and R$^7$, R$^8$, R$^9$, R$^{10}$, R$^{11}$, and R$^{12}$ represent hydrogen.

5. The leuco phenazine dye of claim 1 wherein R$^1$ represents $R^2$ represents 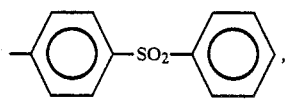, 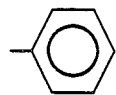
$R^3$, $R^4$, $R^5$, $R^6$ represent alkyl groups having 1 to 4 carbon atoms, and $R^7$, $R^8$, $R^9$, $R^{10}$, $R^{11}$, and $R^{12}$ represent hydrogen.
* * * * *

UNITED STATES PATENT AND TRADEMARK OFFICE
CERTIFICATE OF CORRECTION

PATENT NO. : 4,889,932

DATED : DECEMBER 26, 1989

INVENTOR(S) : ALAN G. MILLER

It is certified that error appears in the above-identified patent and that said Letters Patent is hereby corrected as shown below:

Col. 1, line 35, "Yellow" should be --yellow--.

Col. 2, line 62, "1 carbon" should be --14 carbon--.

Col. 3, line 39, Below formula 2. insert --3. phenyl--.

Col. 6, line 4, After "the" insert --image.--.

Col. 8, line 56, "1-C 13," should be --1-13,--.

Col. 13, line 33, "oenzo" should be --benzoyl leuco--.

Col. 13, line 41, "$R_{10}, R^{11}$," should be --$R^{10}, R^{11}$,--.

Col. 14, line 7, "C." should be --C). A--.

Col. 17, line 57, "$-SO_2R_{17}$" should be -- $-SO_2R^{17}$ --.

Col. 17, line 62, "$R_2$" should be --$R^2$--.

Col. 18, line 21, "$R_3, R_4, R_5$ and $R_6$" should be --$R^3, R^4, R^5$ and $R^6$--.

UNITED STATES PATENT AND TRADEMARK OFFICE
CERTIFICATE OF CORRECTION

PATENT NO. : 4,889,932

DATED : DECEMBER 26, 1989

INVENTOR(S) : ALAN G. MILLER

It is certified that error appears in the above-identified patent and that said Letters Patent is hereby corrected as shown below:

Col. 18, line 32, "$R_{11}$" should be --$R^{11}$--.

Signed and Sealed this

Twenty-fifth Day of June, 1991

*Attest:*

HARRY F. MANBECK, JR.

*Attesting Officer*

*Commissioner of Patents and Trademarks*